(12) United States Patent
Steegers et al.

(10) Patent No.: US 9,095,680 B2
(45) Date of Patent: Aug. 4, 2015

(54) GUIDE WIRE FIXATION

(75) Inventors: Anselm Steegers, Rottenburg (DE); Oliver Schuler, Jungingen (DE)

(73) Assignee: JOLINE GMBH & CO. KG, Hechingen (DE)

( * ) Notice: Subject to any disclaimer, the term of this patent is extended or adjusted under 35 U.S.C. 154(b) by 413 days.

(21) Appl. No.: 13/424,594

(22) Filed: Mar. 20, 2012

(65) Prior Publication Data

US 2012/0253320 A1    Oct. 4, 2012

Related U.S. Application Data

(63) Continuation of application No. PCT/EP2010/063797, filed on Sep. 20, 2010.

(30) Foreign Application Priority Data

Sep. 21, 2009  (EP) .................................. 09170875

(51) Int. Cl.
*A61M 25/00* (2006.01)
*A61M 25/01* (2006.01)
*A61M 25/09* (2006.01)

(52) U.S. Cl.
CPC ....... *A61M 25/01* (2013.01); *A61M 2025/0177* (2013.01); *A61M 2025/09116* (2013.01); *A61M 2025/09125* (2013.01)

(58) Field of Classification Search
CPC ............. A61M 25/01; A61M 25/0172; A61M 2025/0177; A61M 2025/0178; A61M 2025/0188; A61M 2025/09116; A61M 2025/09125

USPC ............. 600/585; 604/158, 164.01, 174–180, 604/528; 606/108
See application file for complete search history.

(56) References Cited

U.S. PATENT DOCUMENTS 5,255,690 A    10/1993  Keith et al.
5,338,313 A *  8/1994   Mollenauer et al. .......... 604/249
(Continued)

FOREIGN PATENT DOCUMENTS

EP      0718004        6/1996
WO      01/24865       4/2001
WO      2005/072807    8/2005

OTHER PUBLICATIONS

Extended European Search Report mailed Feb. 10, 2010, EP Patent Application No. 09170875.0.

(Continued)

*Primary Examiner* — Aarti B Berdichevsky
*Assistant Examiner* — Bradley Osinski
(74) *Attorney, Agent, or Firm* — Casimir Jones, S.C.

(57) ABSTRACT

The present invention concerns an assembly for inserting a catheter into a body lumen, the assembly comprising a introduction, an elongate fixing element, wherein with its distal end the fixing element is securable to the introduction device, and wherein at the proximal end of the fixing element a clamping device is provided for securing a guide wire in relation to the introduction device. Further, the assembly comprises a catheter comprising means for releasably engaging the clamping unit, wherein by engagement of the means of the catheter with the clamping unit the guide wire is movable through the introduction device and wherein, upon disengagement of the means of the catheter from the clamping unit, the guide wire is non-movably secured relative to the introduction device.

8 Claims, 9 Drawing Sheets

(56) References Cited

U.S. PATENT DOCUMENTS

| | | | |
|---|---|---|---|
| 6,695,818 B2* | 2/2004 | Wollschlager | 604/174 |
| 6,986,749 B2 | 1/2006 | Wollschlager | |
| 7,144,378 B2* | 12/2006 | Arnott | 600/585 |
| 8,603,011 B2* | 12/2013 | Landowski | 600/585 |
| 2002/0169396 A1 | 11/2002 | Wollschlager | |
| 2007/0161969 A1* | 7/2007 | Andersen | 604/533 |

OTHER PUBLICATIONS

International Search Report and Written Opinion mailed Oct. 11, 2010, International Patent Application No. PCT/EP2010/063797.

* cited by examiner

GUIDE WIRE FIXATION

CROSS REFERENCES TO RELATED APPLICATIONS

This application is a continuation of international patent application PCT/EP2010/063797, filed on Sep. 20, 2010, designating the U.S., which international patent application has been published in English language and claims priority from European patent application 09170875.0, filed on Sep. 21, 2009. The entire contents of these priority applications are incorporated herein by reference.

BACKGROUND OF THE INVENTION

The present invention concerns an assembly for introducing a catheter into a body lumen, the assembly comprising an introduction device to be introduced into an aperture of the body lumen, a elongate fixing element having a proximal and a distal end, wherein with its distal end the fixing element is securable to the introduction device and wherein at the proximal end of the fixing element a clamping device is provided, which clamping device comprises a clamping unit for securing a guide wire in relation to the introduction device, and which clamping unit comprises a passageway for the guide wire.

Devices of the above kind are used in all different kinds of interventions for treating body lumens and/or hollow organs such as, for example, the vasculature or the respiratory and gastrointestinal system.

During such interventions, as a first step, an introduction device, for example a guide catheter or a valve is introduced into an entry point of the body lumen to be treated. Then a guide wire is advanced through the introduction device, which functions as an application aid, into the body lumen, whereby the guide wire is placed at the location to be treated inside the body lumen.

In a next step, e.g. a catheter—or any other medical device usable for the specific application—is advanced—or "guided"—via the guide wire to the location to be treated, wherein the catheter is threaded over the guide wire. After placement of the catheter, a medical device provided on the catheter, for example a dilation balloon and/or a stent, is deployed in order to treat the body lumen.

During this entire operation, an unintentional positional shift of the guide wire and the catheter is to be avoided because such positional shift may result in displacement of the guide wire and/or catheter and may therefore result in a loss of access of the target anatomy. In addition, its displacement may lead to damage of the walls of the body lumen to be treated.

In order to avoid such undesired shifting of the guide wire, prior art document WO 2005/072807 A1 describes a device for securing one or more guide wires or intravascular catheters in relation to a haemostatic valve assembly. In this connection, the haemostatic valve assembly, comparable to a guide catheter for treatment of the respiratory system, in particular of the sinus paranasales, serves as the introduction device for the guide wire and the catheter into the body lumen. The device comprises a short bracket, onto which a clamping unit is attached, keeping the haemostatic valve and the clamping unit spatially defined to each other.

The clamping unit comprises actuatable clamping mechanisms that allow the surgeon to lock guide wires or catheters guided through these clamping mechanisms relative to their respective longitudinal positions with respect to the haemostatic valve and, hence, the body lumen.

The device disclosed in WO 2005/072807 has the disadvantage that it is not possible to hold a guide wire while a catheter is being advanced through the haemostatic valve. Undesired positional changes of the guide wire, however, occur predominantly during this phase of the operation, since such positional changes are often resulting from the friction between the guide wire surface and the inner walls of the catheter lumen. Hence, the guide wire may be shifted in distal direction when the catheter is introduced into the body lumen. Further, the clamping of a guide wire or catheter in relation to a certain longitudinal position requires an additional handling step by the operator.

Another prior art document, WO 01/24865, discloses a device for handling at least one guide wire, in order to guide an invasive medical instrument. The device comprises a fixing arm, which can be fixed to an introduction valve, and a clamping device attached to the fixing arm. The clamping device disclosed in WO 01/24865 consists of a clamping sleeve arrangement, which in turn consists of a clamping sleeve and a screw sleeve, which can be—in a rotatable manner threaded over the clamping sleeve to clamp the guide wire placed therein.

This device has the disadvantage that is complicated to handle, since for fixation of the guide wire the clamping sleeve arrangement has to be handled with both hands of the operating person, before, e.g., a catheter may be introduced and advanced over the fixed guide wire into the body lumen to be treated.

SUMMARY OF THE INVENTION

In view of the above, it is an object of the present invention to improve the known devices, such, that a guide wire can be locked relative to a certain longitudinal position even during the insertion of a guide wire. At the same time, it is desirable for the guide wire fixing mechanism to be easily manageable, from a technical and operatable point of view.

According to one aspect of the invention, there is provided an assembly for introducing a catheter into a body lumen, the assembly comprising an introduction device to be introduced into an aperture of the body lumen, a elongate fixing element having a proximal and a distal end, wherein with its distal end the fixing element is securable to the introduction device and wherein at the proximal end of the fixing element a clamping device is provided, which clamping device comprises a clamping unit for securing a guide wire in relation to the introduction device, and which clamping unit comprises a passageway for the guide wire, which is configured such that it comprises a catheter, having a proximal end and a distal end, wherein the catheter comprises at its proximal end a means for releasably engaging the clamping unit, wherein by engagement of the means with the clamping unit the guide wire is movable through the introduction device and wherein upon disengagement of the means from the clamping unit the guide wire is non-movably secured relative to the introduction device.

A "catheter", according to the invention, is an elongate tube that can be inserted into a body cavity, duct or vessel. Catheters thereby allow drainage, injection of fluids or access by surgical instruments, and can be used, e.g. to deploy a medical device such as an endoluminal prosthesis or a dilation balloon. When being configured as a balloon catheter, the catheter comprises an inflatable balloon for dilating the body lumen to be treated and/or a balloon-expandable endoluminal prosthesis which, in these cases, is crimped on the balloon's exterior.

A "body lumen" or "body cavity" within the scope of the present invention may be any lumen or cavity inside the human or animal body, for example a lumen of the vasculature, e.g. a vessel, the digestive tract, and the respiratory- or genitourinary system, or a duct.

Throughout the following, the description of the invention mainly refers, as an exemplary embodiment for its application, to the respiratory system, in particular the sinus paranasalis, without, however, restricting the scope of the present invention to the sinus paranasalis or other parts of the respiratory system.

In the scope of the present invention, an "introduction device" is meant to comprise any device adjusted to forming a permanent or temporary entry point into a body lumen, and—thus—comprises a lumen, which may be central or not, or a groove for giving passageway to the body lumen. For example, an introduction device may be a guide catheter, which can be placed in the nares for providing access to the sinus paranasales. Alternatively, an introduction device may be a trocar, which can be partly inserted through an incision into, for example, the thoracic cavity. Moreover, an introduction device may be a hemostatic valve assembly, partly inserted through an incision into a patient's vasculature and providing access thereto.

Within the scope of the present invention, a "guide catheter" is understood to be a catheter of short to intermediate length, the catheter comprising a relatively stiff hollow tube adjusted for insertion into a body lumen. Such guide catheter is used for delivering to the point of entry into a tighter body lumen a guide wire and a catheter to be inserted into said body lumen via said guide wire.

The guide catheter, at its proximal end, may comprise a valve assembly, such as a valve of the tuohy-borst type. At its distal end, the guide catheter may either be straight or may, preferably, comprise a curve, such as a guide catheter usually employed in Sinuplasty.

Within the scope of the present invention, a "guide wire" is a long, slender and relatively flexible wire, which is used to gain and maintain access to the body's narrow passageways. It can be used for catheter placement, for example according to the Seldinger-technique. For this purpose, the guide wire is inserted into a body lumen, for example a blood vessel, prior to advancing a catheter. The catheter is then advanced into the blood vessel, whereby it is guided by the guide wire which—thereby—gets accommodated in the lumen or the lumina of the catheter.

Thus, such catheters to be guided by guide wires may be either of the "over the wire-" or the "monorail-"type. Over the wire catheters comprise an internal lumen, extending over the entire length of the catheter, which lumen is provided for accommodating said guide wire. By contrast, monorail catheters comprise only a relatively short guide wire lumen, provided at the distal end of the catheter. While monorail-catheters are comparably easy to use and require shorter guide wires, over the wire catheters are generally regarded to be safer in use. This is due to the fact that the catheter is kept in place over its entire length by the guide wire comprised in its interior lumen.

It is understood that the catheter according to the present invention may be either an over the wire or a monorail-catheter.

A "clamping device" within the scope of the present invention is understood to be a device or unit for locking or fixing an elongated structure, for example a guide wire or catheter, relative to a spatially defined position in one or, preferably, any degree of freedom, especially in axial direction. For this purpose, the clamping device usually comprises a port, recess or lumen adjusted for accommodating therein the elongated structure of the guide wire. The port, recess or lumen may, in this connection be open only in axial direction with respect to the elongated structure comprised therein or may also be laterally open in order to allow the lateral insertion and retrieval of the elongated structure. Further, the clamping device usually comprises a unit for at least temporarily fixing the elongated structure relative to a certain position with respect to at least one degree of freedom. This unit, according to the present invention, is referred to as "clamping unit".

The expression "proximal", with respect to a catheter, describes the direction towards an operator handling the catheter, while the expression "distal" describes the direction towards the catheter tip, facing away from the operator. Thus, the proximal end of a structure represents the end which is nearer to the operator handling the structure, and the distal end represents the end which is opposed to the proximal end and, thus, farther away from the operator.

An "elongate fixing element" or a "longitudinally extending fixing element" is any element having an elongate design and being suitable for being secured with one of its end to the introduction device. The fixing element may represent a fixing arm or elongate fixing handle.

"Clamping jaws" according to the invention are any opposable structures, whereby at least a portion of their surfaces can be moved into direct proximity of one another to clamp anything that is located there between.

In the novel assembly, the introduction device and the clamping device are—by means of the fixing element—arranged in a spatially defined distance to one another. The length of the elongate fixing arm is dimensioned such, that in between the introduction device and the clamping unit of said clamping device, a certain distance is provided, which distance is sufficient to accommodate, e.g., a catheter handle of the kind described hereinafter and a portion of catheter tube of a length sufficient for performing a feed motion positioning the catheter tip or, respectively, a balloon provided on the catheter at the position to be treated inside the body lumen.

Hence, the catheter can be movably arranged in a central lumen of said introduction device, which comprises a lumen for accommodating the catheter, and the catheter, or rather a means attached to it, is proximally enclosed by the clamping device and distally enclosed by the introduction device.

According to the invention, the clamping unit comprises a passageway for the guide wire, and contains in a preferred embodiment a bore for guiding the guide wire there through.

At the catheter's proximal end, the means releasably engages the clamping device, in particular the clamping unit of said clamping device. The catheter—per definitionem—comprises a central lumen which carries the guide wire in a movable manner. With the engagement of the catheter means with the clamping device, a passageway through the clamping unit is provided the diameter of which is larger than the diameter of the guide wire. The guide wire, which enters the passageway of the clamping unit on the proximal end of the clamping unit, i.e. the end which is nearer to the operating person, and is—through the catheter engaging means—guided into and carried in the catheter lumen. In this configuration, the guide wire is—due to the passageway in the clamping unit—movable in the catheter lumen in axial direction with respect to the assembly and, respectively, the body lumen.

Hence, while the catheter is engaged with the clamping unit, the guide wire can be advanced through the catheter and into the body lumen and be positioned in the part of the body lumen to be treated. In order to fix the guide wire and to inhibit its displacement in axial direction, the catheter is shifted from its initial position in distal direction, whereupon the catheter means disengages from the clamping unit. Upon disengagement of the catheter means from the clamping unit, the clamping unit changes its configuration, such, that the passageway through the clamping unit is tightly narrowed and the guide wire is locked or fixed in its position with respect to the longitudinal axis of the assembly and the body lumen. Hence, when the catheter is further advanced into the body lumen via the guide wire, the friction between guide wire and catheter no longer results in a longitudinal shift or displacement of the guide wire. This effect is achieved without an additional handling step to be performed by the operator.

The terms "Catheter engaging means" or "catheter means for engaging" are alternatively used, and mean any element or structure of a catheter, that forms either an integral part of the catheter or is attached to it as a separate element, and by means of which the catheter can be engaged with the clamping unit.

According to one aspect of the invention, the clamping unit comprises at least two clamping jaws for fixing the guide wire, preferably at the distal end of the clamping unit, wherein the at least two clamping jaws each comprise a first and a second end, wherein at least the two clamping jaws are connected on either the first or the second ends to form connected ends, and wherein on the respective other end the clamping jaws are separable from one another by frictional engagement of the means of the catheter.

This embodiment has the advantage that with one step, the guide wire can be clamped between the at least two clamping jaws upon disengagement of the catheter means from the clamping unit. In other words, to place the guide wire in the body lumen, the means of the catheter are engaged with the clamping unit, such, that the two clamping jaws are forced to separate from one another to releasably engage with the catheter means. Thus, a passageway though the clamping unit is provided which has a larger diameter than the guide wire. In this position, the two clamping jaws clamp the catheter means—and prevent the catheter from being moved in axial direction—and the guide wire can be freely moved, i.e. without friction, in and through the catheter lumen into the body lumen. To introduce the catheter into the body lumen without displacing the guide wire, the means of the catheter are disengaged from the two clamping jaws upon which they close the passageway and clamp the guide wire guided there through. The catheter can now be introduced into the body lumen, while the guide wire stays stably fixed. It is to be understood, that within the scope of the present invention two or more clamping jaws may be provided, wherein it lies within the skill and knowledge of a person skilled in the art when clamping units with two or clamping units with more than two clamping jaws are to be considered and designed. Presently and in the following examples, when it is referred to two clamping jaws, also embodiments with more than two clamping jaws are comprised.

The expression "frictional engagement" as it is used in connection with the present invention is meant to comprise any engagement of the means of the catheter with/in the clamping unit, by means of which the clamping jaws are spread through the mere introduction of the means of the catheter into/between the clamping jaws. Thus, the clamping jaws are forced apart by moving the engagement means at least partially between the clamping jaws, wherein the engagement means of the catheter frictionally interact with the clamping jaws, or rather with a surface of the clamping jaws, and are, thus, being held/clamped between them through friction and pressure exerted by the clamping jaws on the means.

Thus, the clamping unit can be actuated by engagement and disengagement of the means of the catheter in a very reliable and efficient manner.

Moreover, such simple mechanism is easy to sterilize and can be produced in a very cost-efficient manner.

According to a preferred refinement, the clamping jaws may be separated/expanded by elastic deformation of the one or more material bridges connecting the at least two jaws at one of their ends, respectively. Alternatively, the clamping jaws may be separated by means of a joint, hinge or any other kind of fitting.

According to another embodiment, the clamping jaws are separable from one another by elastic deformation of one or more spring elements.

The spring elements may be provided in the clamping unit and connect the clamping jaws with the clamping unit. Upon engaging of the catheter means with the clamping jaws, they are—against the spring pressure exerted on the clamping jaws—forced to separate from one another and to provide a passageway for the guide wire where it is freely movable.

The clamping jaws have the advantage that they can at least in part be spread or expanded or separated by the catheter means engaging the clamping unit. Hence, the engagement and disengagement of the catheter means with the clamping unit is mechanically directly coupled to the opening or closure of the clamping jaws, which means that a minimal number of moving parts is required.

The clamping jaws thus comprise an inner surface, which engages (and clamps) either the catheter means upon or—upon disengagement of the catheter means from the clamping unit—the guide wire that is guided through the clamping unit and the catheter lumen. Hence, the frictional engagement between the inner surface of the clamping jaws and the means holds the catheter in position, or the frictional engagement of the inner surface of the clamping jaws and the guide wire, that upon disengagement of the catheter means comes into direct contact with the inner surfaces of the clamping jaws.

In a further embodiment, the clamping jaws are provided at the distal end of the clamping unit, where the catheter means engages it.

In a further embodiment, the clamping jaws may—at their inner and clamping surface—comprise a recess for engaging the catheter means. Hence, when the means are brought into frictional engagement with the clamping jaws, they engage the recess, separating the clamping jaws until the space in between the opposing surfaces of the jaws is sufficient to let the distal end of the catheter pass in between the jaws. When comprised in between the jaws, the means are frictionally engaged and, hence, held tight with respect to the clamping unit.

This way, the catheter can be held in position with respect to the clamping device in a mechanically relatively simple and straightforward manner. Further, in this connection no additional movable parts are required for holding the catheter, facilitating the design and hence, the production of such device and making easier its sterilization.

In a refinement of the invention, it is preferable if the clamping jaws comprise at their inner/clamping surfaces a knurled or undulated surface.

Such clamping surfaces are configured such that, upon disengagement of the means from the clamping unit, they frictionally engage/clamp the guide wire. By providing knurled/undulated clamping surfaces, the frictional engagement between the clamping surfaces and the guide wire/the catheter means can be increased.

Alternatively or in addition, the clamping surfaces may be coated or comprised of a material triggering high friction, like for example, an elastic material selected from the group comprising an elastomer and rubber.

Hence, the guide wire can easily and efficiently be secured with respect to its longitudinal position, reducing the risk for the guide wire slipping through clamping surfaces during catheter advancement.

In yet another refinement of the invention it is preferable if the clamping jaws can be shifted with respect to the clamping unit by elastic deformation of one or more material bridges connecting the clamping jaws to the clamping device.

In this embodiment, the elastic force of the material comprising the clamping unit is used for exerting frictional engagement of the clamping jaws on the catheter, when the catheter is engaged into the clamping unit, or on the guide wire, when the catheter is disengaged from the clamping unit. Hence, shifting the clamping jaws with respect to the clamping unit is achieved without additional movable parts. This, as described before, leads to a decrease in production costs and makes sterilization procedures of the device easier.

According to another aspect of the invention, alternatively or in addition, the clamping jaws can be shifted/separated with respect to the clamping unit by elastic deformation of one or more spring elements or hinges provided in between the clamping jaws—or rather at one of their ends—and the clamping device.

Such spring elements may be elastic parts, configured to exert counterpressure upon their elastic deformation. For example, spring elements may be springs comprised of steel.

In this embodiment, instead of the material elasticity of the clamping unit, separate spring elements are responsible for compressing the clamping jaws against the guide wire and/or pressing the holding surfaces against the catheter.

This configuration has the advantage that such a device is less prone for fatigue failures occurring, for example, in a hinge region repeatedly elastically deformed. Hence, the safety of the device can be improved. Moreover, the storability of such a device is enhanced due to the avoidance of fatigue failure resulting from chemical alteration of, for example, the hinge region's material.

According to yet another embodiment, the means of the catheter for engaging the clamping unit comprise a proximal and a distal end, wherein the proximal end is adapted for releasably engaging the clamping unit, and wherein via the distal end the means are releasably or non-releasably attached to the catheter.

Thus, the means for engaging are either releasably attached to the catheter, and are thus formed of at least two different pieces, or are otherwise integrally formed with the catheter so that the means may not be separated from the catheter.

According to another aspect of the invention, the proximal end of the means of the catheter for releasably engaging the clamping unit comprises a handling portion of the catheter releasably or non-releasably attached to the catheter. In particular, the means for engaging, or rather the handling portion, may represent or comprise a ring or half-ring shaped element for handling the catheter.

In that way, a convenient handling grip is provided that may be integrally formed with the catheter or may be releasably attached to the catheter; also, this handling portion serves two functions, namely to easily handle or grip the catheter at this site, and eventually to move it in distal direction by gripping the handling portion and by disengaging the means from the clamping unit. On the other hand, the handling portion serves for engaging the clamping jaws/clamping unit in order to force the clamping jaws apart.

Further, it is preferred if the introduction device is a guide catheter adjusted for use in sinuplasty, i.e. for the dilation of the ostia of the paranasal sinuses.

With sinuplasty, or rather balloon sinuplasty, blocked sinuses of patients suffering from sinusitis are treated with a catheter-based system. During sinuplasty, a small, flexible, sinus balloon catheter is used to open up blocked sinus passageways, in order to restore normal sinus drainage. Upon inflating the sinus balloon, the walls of the passageways are restructured and widened while the integrity of the sinus lining is maintained.

In this connection, it is advantageous that sinuplasty requires only feed motions of minor extent. Hence, the assembly, even though comprising all necessary parts for inserting a catheter into a body lumen, can be kept, as a hole, relatively short and compact.

According to another aspect of the present invention, the introduction device comprises a valve for sealing the central channel of the introduction device.

Such valve may be, for example, a haemostatic valve, for example of the tuohy-borst type. Hence, a tight seal between the interior of the body lumen and the exterior can be formed. Such a tight seal is of advantage whenever an elevated pressure is present inside the body lumen. In this connection, for example during endovascular operations, a tight seal prevents the outflow of blood from the central channel.

Alternatively, such valve may be of relevance whenever a body lumen is to be inflated by elevated pressure, for example during endoscopic operations within the thorax. Moreover, such seal may prevent the outflow of flushing liquid and mucus from the body lumen during flushing of the lumen.

According to another aspect of the invention, a clamping device is provided for securing a guide wire in relation to a body lumen, the clamping device comprising a fastening element for fastening said clamping device to an introduction device, a clamping unit for clamping said guide wire, and a elongate fixing element connecting said fastening element and said clamping unit, which clamping device is configured such that said clamping unit comprises two clamping jaws which in a first position are separable from one another by frictional engagement of a catheter means and hold the catheter means and which in a second position upon disengagement of the catheter means clamp the guide wire.

Such clamping device, while being configured to be combined with a number of different introduction devices, such as haemostatic valves, trocars, guide catheters or similar devices, that provide access to a body lumen, is adjusted for securing, with respect to said introduction device, a guide wire.

The clamping device therefore enables the use of the inventive principle also in combination with a variety of other introduction devices. Hence, the advantages described hereinabove can also be achieved when using such introduction devices.

According to yet another aspect of the invention, a method for inserting a catheter into a body lumen is provided, in which method the assembly or the clamping device according to the invention and described herein above is used, the method comprising the steps of a) inserting into an aperture of the body lumen an introduction device of the assembly, b) inserting a guide wire through assembly into the body lumen, and c) advancing a catheter into the body lumen via the guide wire, wherein, during step c), a clamping device of the assembly is actuated by disengagement of catheter means from the clamping device, securing the guide wire in relation to the body lumen.

The advantage of this method is that the guide wire can be secured to an axial position even during advancement of the catheter into the body lumen. Further, the fixing of the guide wire relative to its longitudinal position during catheter advancement can be achieved without additional handling steps.

It is understood that the features described above and those still to be specified below fall within the scope of the present invention not only in the respectively specified combinations, but also in other combinations or on their own.

BRIEF DESCRIPTION OF THE DRAWINGS

Several embodiments of the invention are illustrated in the figures and explained in more detail in the following description. In the figures.

DESCRIPTION OF PREFERRED EMBODIMENTS

Figure 1:
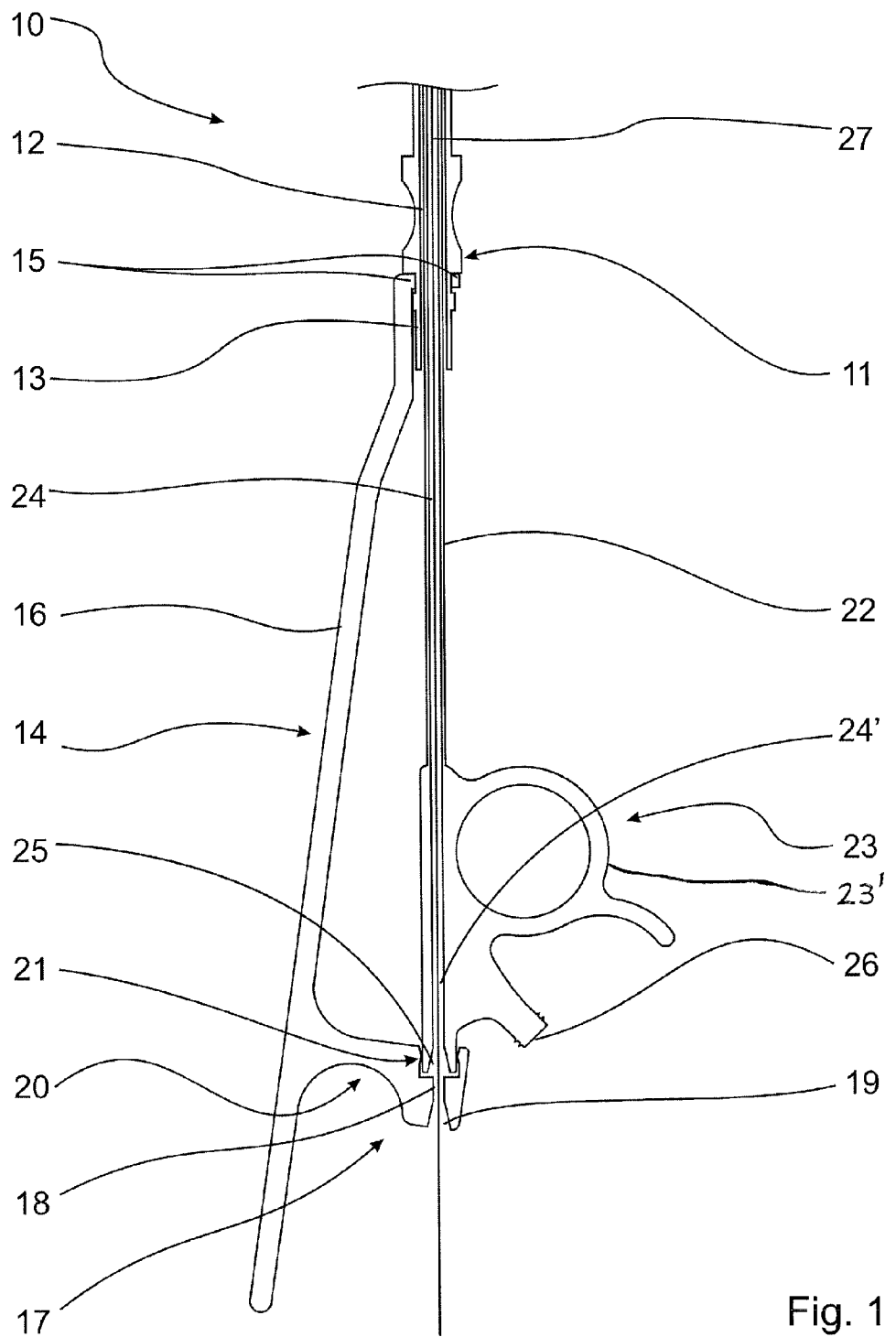
FIG. 1 shows a schematic drawing of a side view of an assembly according to a first embodiment, with the catheter being engaged with the clamping unit.

FIG. 1, like the following FIGS. 2 to 14, is a schematic drawing of an embodiment of the assembly according to the invention, wherein the drawings are not drawn to scale. An assembly 10 is shown, comprising a guide catheter 11, functioning as introduction device, with a central channel 12 and a valve 13. Further, the assembly comprises a clamping device 14 attached to said guide catheter 11 via fastening element 15. The clamping device 14 comprises an elongate fixing element 16, that has the design of a fixing arm, and a clamping unit 17, the fixing element arranged in between and connecting said fastening element 15 and said clamping unit 17, providing a fixed distance between said clamping unit 17 and said guide catheter 11.

The clamping unit 17 comprises a clamping lumen 18, which in the embodiment shown in FIG. 1, proximally widens to form an opening 19 having the shape of a feed hopper. Further, the clamping unit 17 comprises a hinge region 20 adjusted for elastic deformation of said clamping unit 17, allowing clamping jaws 21, connected to clamping unit 17 via material bridges comprising the hinge region 20, to be separated from one another.

Movably held within said central channel 12 of guide catheter 11, a catheter 22 having a catheter lumen 24 is provided, which catheter 22 at its proximal end comprises an engaging means 23, which in FIG. 1 has the design of a grip or handle comprising a ring-shaped element 23', and which engaging means 23 engages clamping unit 17. The Catheter engaging means 23 forms part of or is attached to the catheter 22 and, therefore, also comprises a lumen 24'; proximal end 25 of the lumen 24' of the catheter engaging means 23 widens in order to form a feed hopper. Further, the catheter 22 comprises a side arm 26 with a connector providing an access or a port. By means of this connector, for example, an inflation gas may be fed into the catheter for inflating a balloon (not shown) provided on the distal end of catheter 22.

The assembly of FIG. 1 is shown in its initial configuration, at the beginning of an medical intervention/application.

In this configuration or position, a guide wire 27 has been advanced through the opening 19 of the clamping unit 17 into clamping lumen 18 and further, through the opening 25 of the catheter engaging means 23, into the lumen 24' and 24 of catheter engaging means 23 and of the catheter 22, respectively, and is also guided into and carried in central channel 12 of guide catheter 11.

In the further steps of the medical intervention, guide wire 27 is introduced via guide catheter 11 into a body lumen (not shown), where it is positioned at a location to be treated, which can, e.g., be monitored by x-Ray or via endoscopic means.

Figure 2:
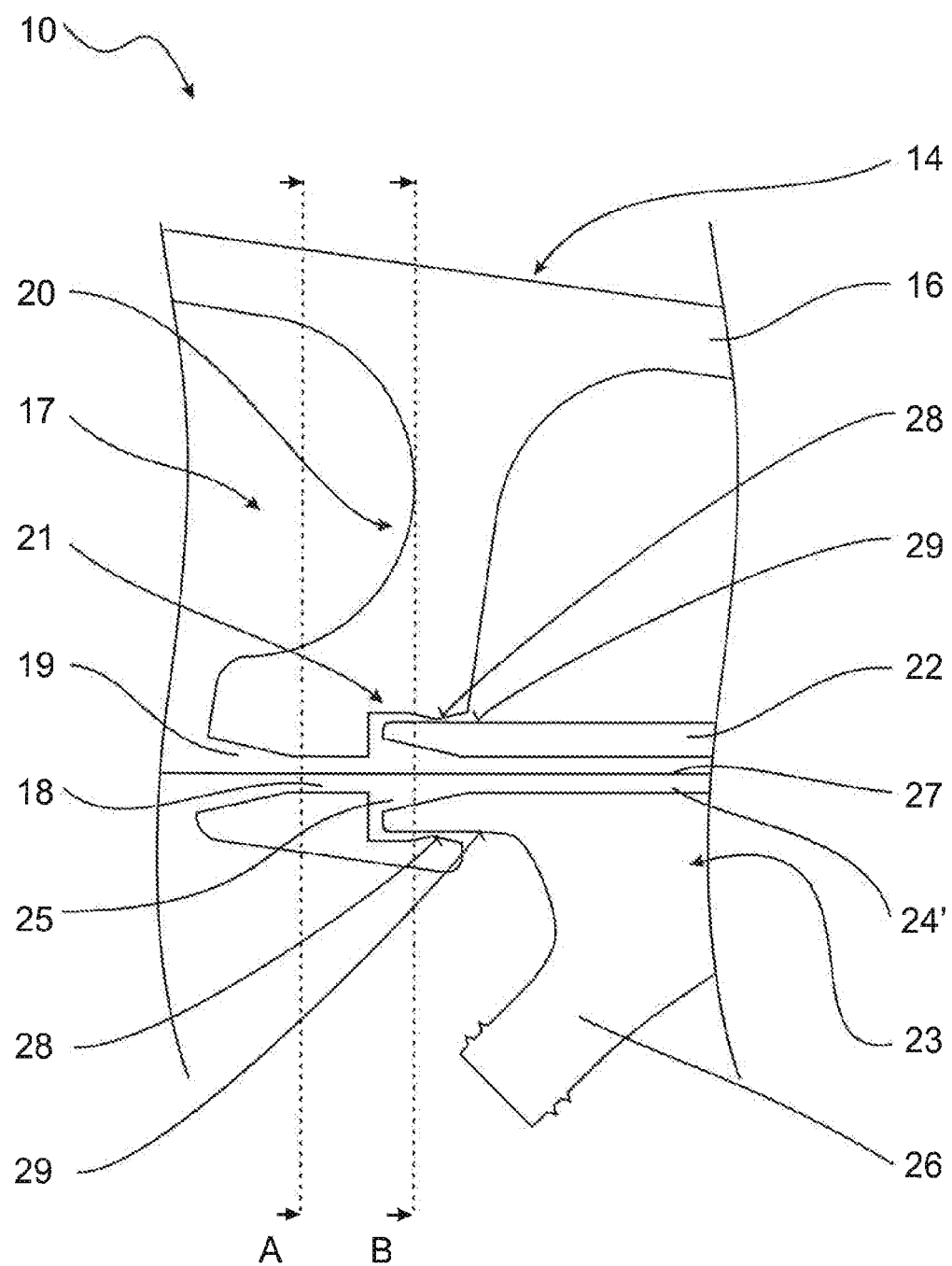
FIG. 2 shows an enlarged schematic cut-out of the part of the assembly of FIG. 1, where the catheter means engages the clamping unit.

In order to achieve correct positioning of the guide wire 27, the guide wire 27 has to be freely movable through the assembly 10 with respect to its longitudinal axis FIG. 2 shows an enlarged side view of the part of assembly 10 shown in FIG. 1, where the catheter means 23 engages the clamping unit 17.

Clamping unit 17, with the surfaces 28 of clamping/holding jaws 21, frictionally engages outer surfaces 29 of the catheter engaging means 23. By means of this frictional engagement, catheter 22, which is attached to the catheter engaging means 23, is firmly but releasably held within clamping unit 17. In this configuration, clamping jaws 21 are spread/separated by the catheter engaging means 23 engaging the clamping jaws 21 (depicted in FIGS. 4 and 5), therefore providing a passageway and leaving open clamping lumen 18, whereby free movement of guide wire 27 along its longitudinal axis is allowed and possible.

Figure 3:
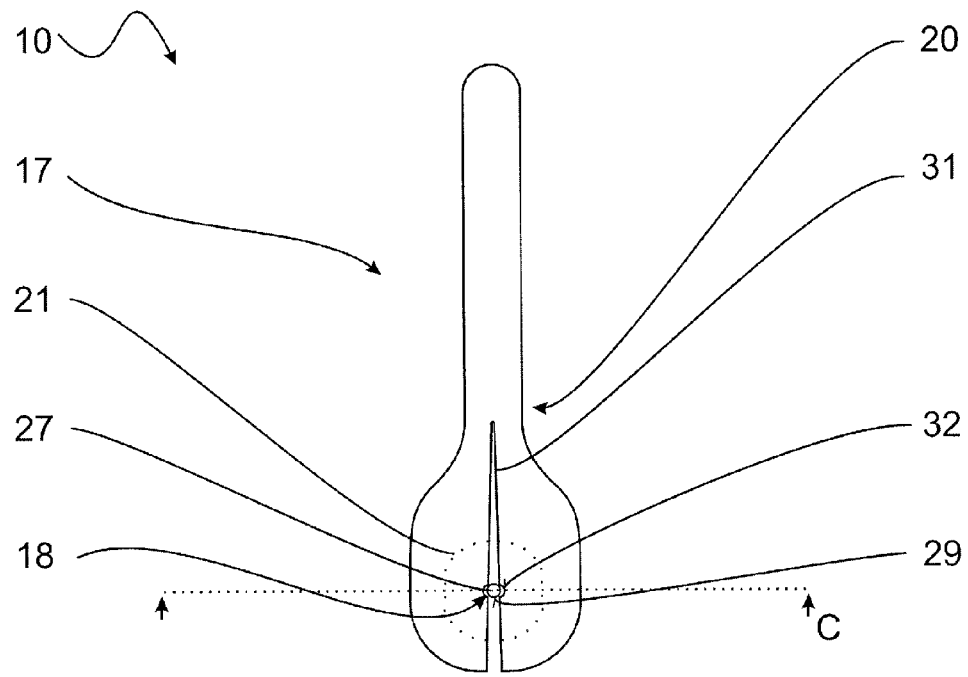
FIGS. 3 and 4 show a schematic drawing of a view along lines A and B as specified in the assembly of FIG. 2, a guide wire being movably held therein.

FIG. 3 shows a view a part of assembly 10 shown in FIG. 2 along line A as indicated in FIG. 2, in particular clamping unit 17 comprising clamping jaws 21, connected to clamping unit 17 via hinge region 20, which is, in the embodiment shown in FIG. 3, a material bridge.

Due to engagement of catheter engaging means 23 with and into clamping unit 17, clamping jaws 21 are separated relative to a imaginary axis 31, leaving open clamping lumen 18. Hence, clamping surfaces 32 of the clamping lumen 18 are detached from surface 33 of the guide wire 27, allowing guide wire 27 to move in longitudinal direction within clamping lumen 18.

Figure 4:
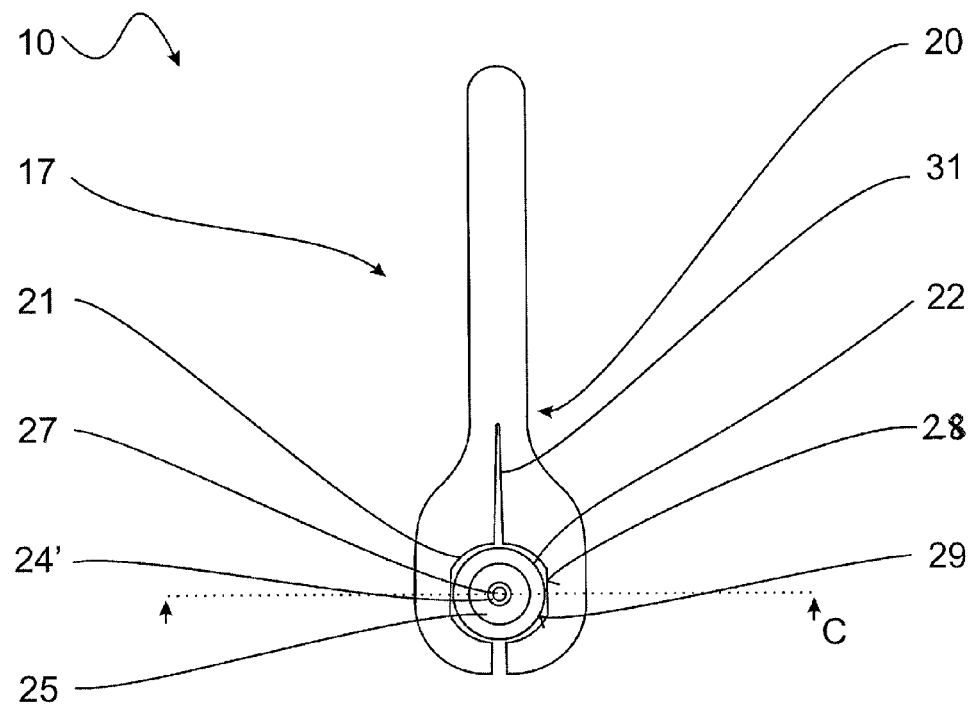

FIG. 4 shows another view of the part of assembly 10 shown in FIG. 2, this time along line B as also indicated in FIG. 2. Here, catheter 22 is shown, engaging with its surface 29 surfaces 28 of the separated clamping jaws 21. Thereby, surfaces 28 and, hence, clamping jaws 21 are pressed apart, parting along imaginary axis 31. The separating of clamping jaws 21 along imaginary axis 31 is achieved by elastic deformation of the material in hinge region 20.

Figure 5:
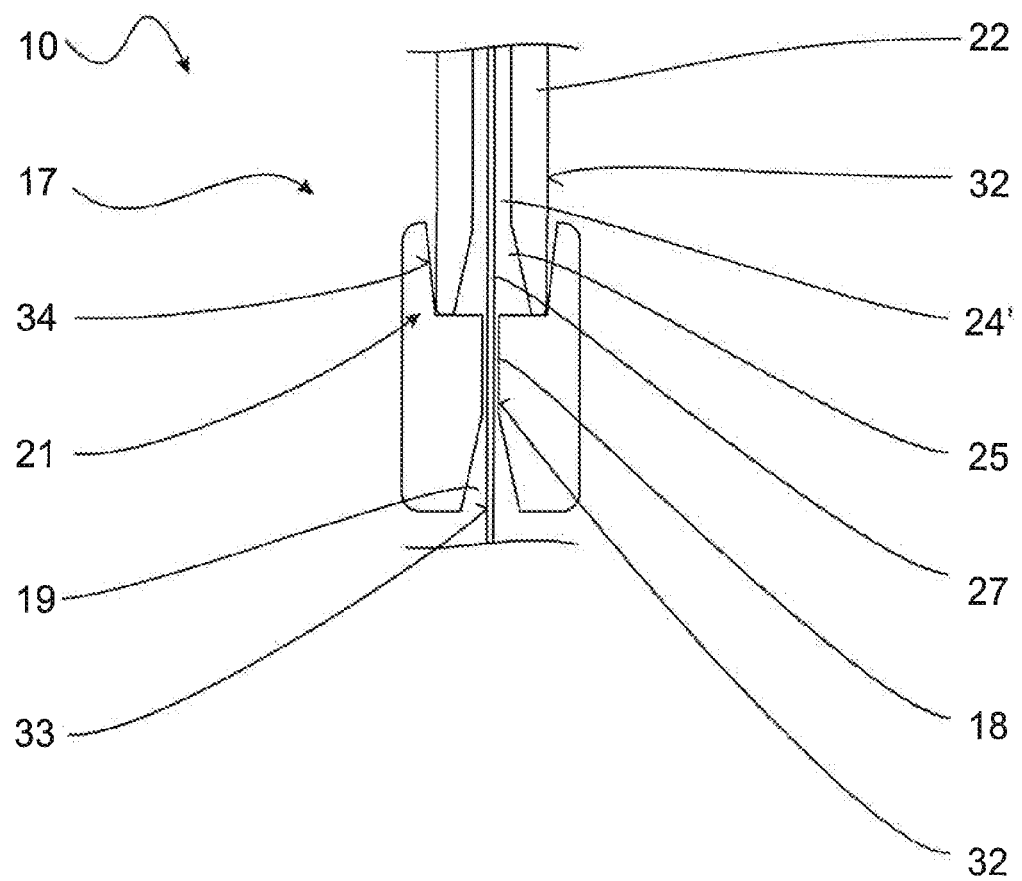
FIG. 5 shows a schematic drawing of the assembly shown in FIG. 1, along line C as indicated in FIGS. 3 and 4.

FIG. 5 shows the clamping unit 17 of the embodiment shown in FIGS. 2 to 4, displaying a view along plane C as indicated in FIGS. 3 and 4.

As can be taken from this figure, surfaces 28 of clamping jaws 21 form a recess, into which catheter engaging means 23 can be introduced to separate clamping jaws 21 from one another. Hence, when catheter 22 is moved in proximal direction (i.e. in the direction of the operating person), the engagement of engaging means 23 with the recess formed in the clamping unit 17 gradually forces apart the clamping jaws 21. As shown in FIG. 5, the proximal end of catheter engaging means 23 abuts against the recess end formed in the clamping unit 17.

Also, FIG. 5 shows that the surfaces 28 of clamping jaws 21 are distanced from the surface 33 of guide wire 27, allowing guide wire 27 to be moved with respect to its longitudinal axis.

When guide wire 27 has been placed within a body lumen at the location to be treated, catheter 22 is advanced into the body lumen and threaded over guide wire 27 to the position to be treated.

Figure 6:
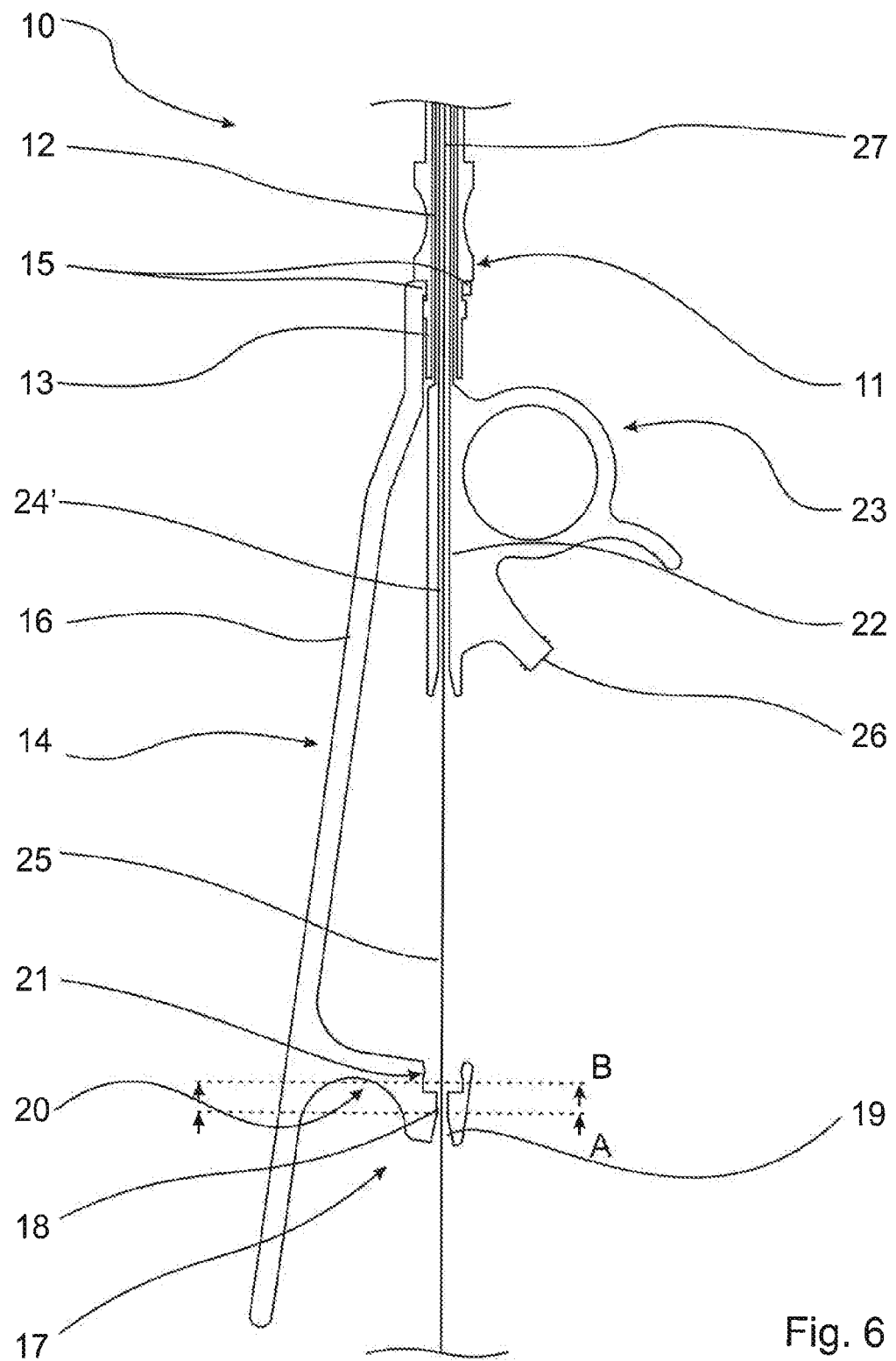
FIG. 6 shows a schematic drawing of the side view of the assembly as displayed in FIG. 1, with the catheter having been being disengaged from the clamping unit.

This situation is shown in FIG. 6.

FIG. 6 shows the same assembly 10 as in FIG. 1, but with catheter 22 having been advanced into a distal position, i.e. away from the operating person and towards the body lumen.

At the beginning of catheter advancement, catheter engaging means 23, and thereby catheter 22, disengages clamping unit 17. Clamping unit 17, when getting disengaged from catheter engaging means 23, clamps and thereby fixes the guide wire 27 to its longitudinal position. This is achieved by the closing and narrowing of the clamping jaws 21 towards one another, since the pressure exerted by the engagement of the engaging means 23 and holding them apart is removed.

Figure 7:
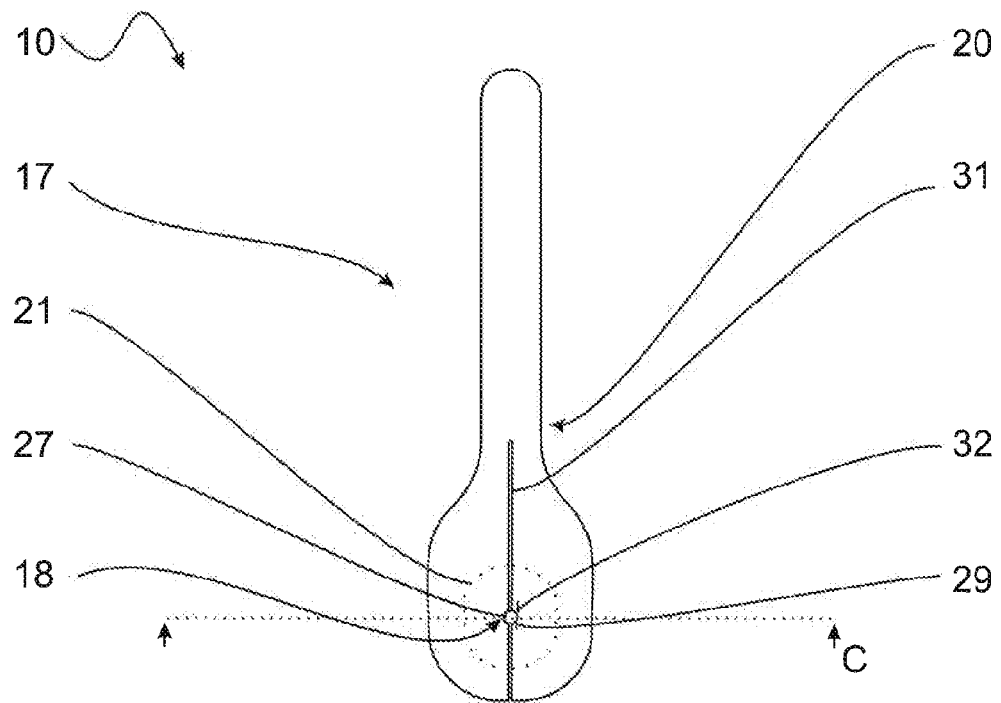
FIGS. 7 and 8 shows a schematic drawing of the assembly as shown in FIG. 6 along lines A and B as indicated in FIG. 6.
Figure 8:
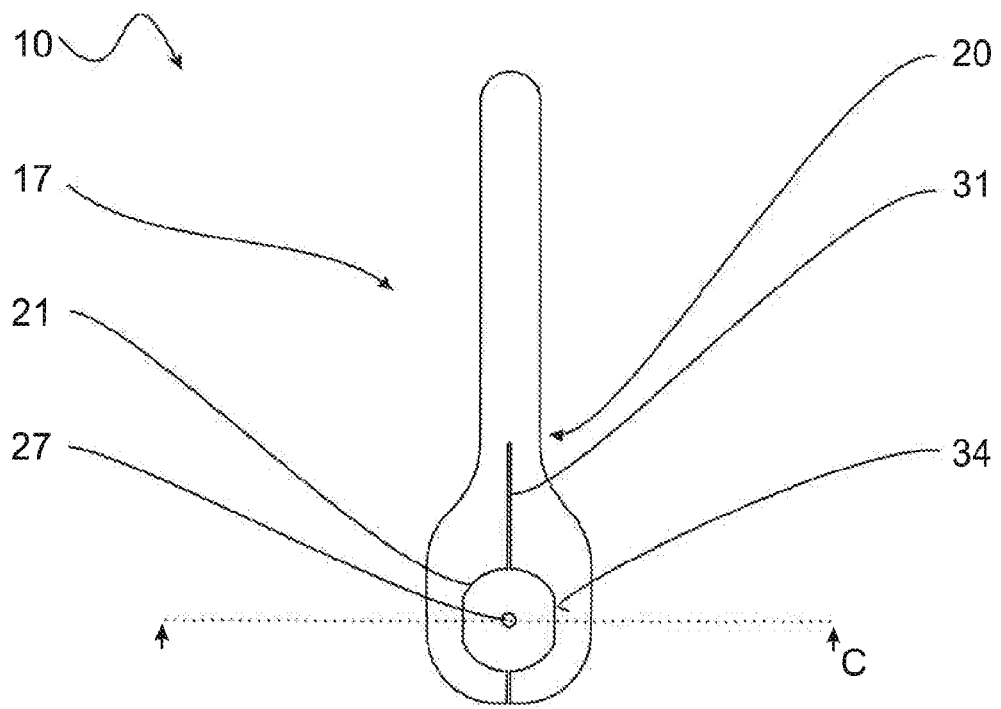

FIG. 7 shows a drawing of the assembly 10 as shown in FIG. 6, i.e. upon disengagement of catheter 22 from clamping unit 17, along line A indicated in FIG. 6, while FIG. 8 a view along line B indicated in FIG. 6.

In this position, clamping jaws 21 are no longer forced apart by engagement of catheter means 23 and, thus, are in a nearly closed position. Surfaces 28 of clamping jaws 22 have nearly closed clamping lumen 18, thereby tightly clamping and fixing guide wire 27 and frictionally engaging its surface 33. Hence, guide wire 27 is firmly locked between the opposing surfaces 28 of clamping jaws 21 and can no longer be moved with respect to its longitudinal axis.

Figure 9:
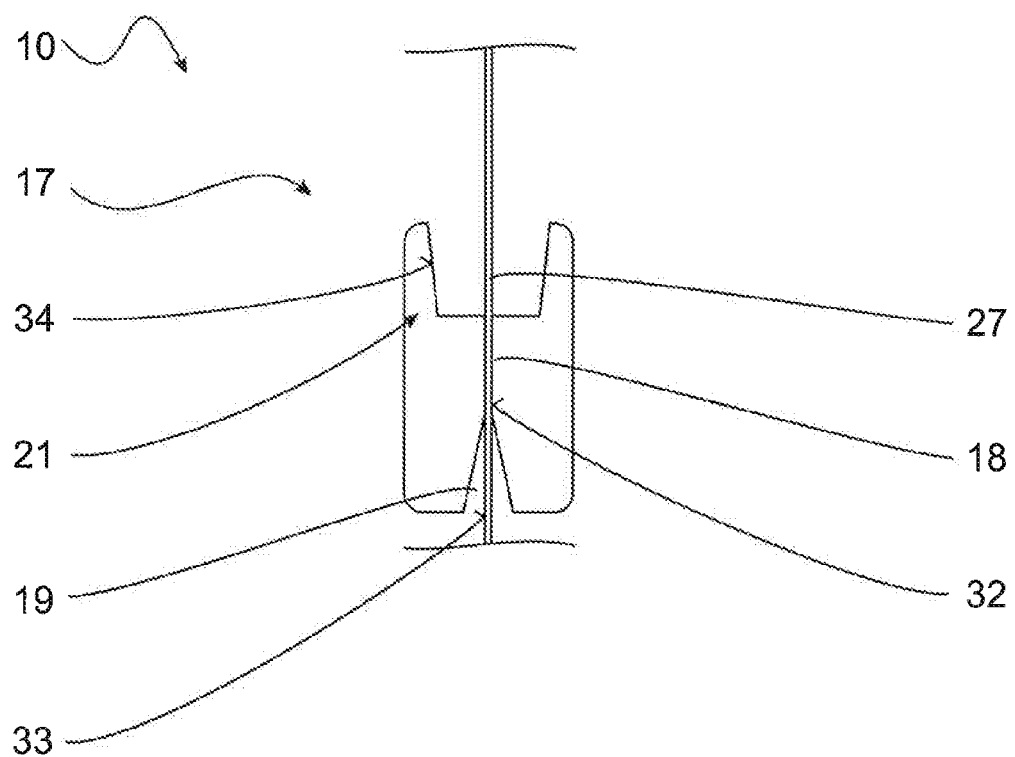
FIG. 9 shows a schematic drawing of the assembly shown in FIG. 6, along line C as indicated in FIGS. 7 and 8.

As shown in FIG. 9, which shows a view along plane C as indicated in FIGS. 7 and 8, surfaces 28 of clamping jaws 21—upon release of catheter engaging means 23 from clamping unit 17—close clamping lumen 18, thereby frictionally engaging at least the lateral sides the surface 33 of guide wire 27.

Figure 10:
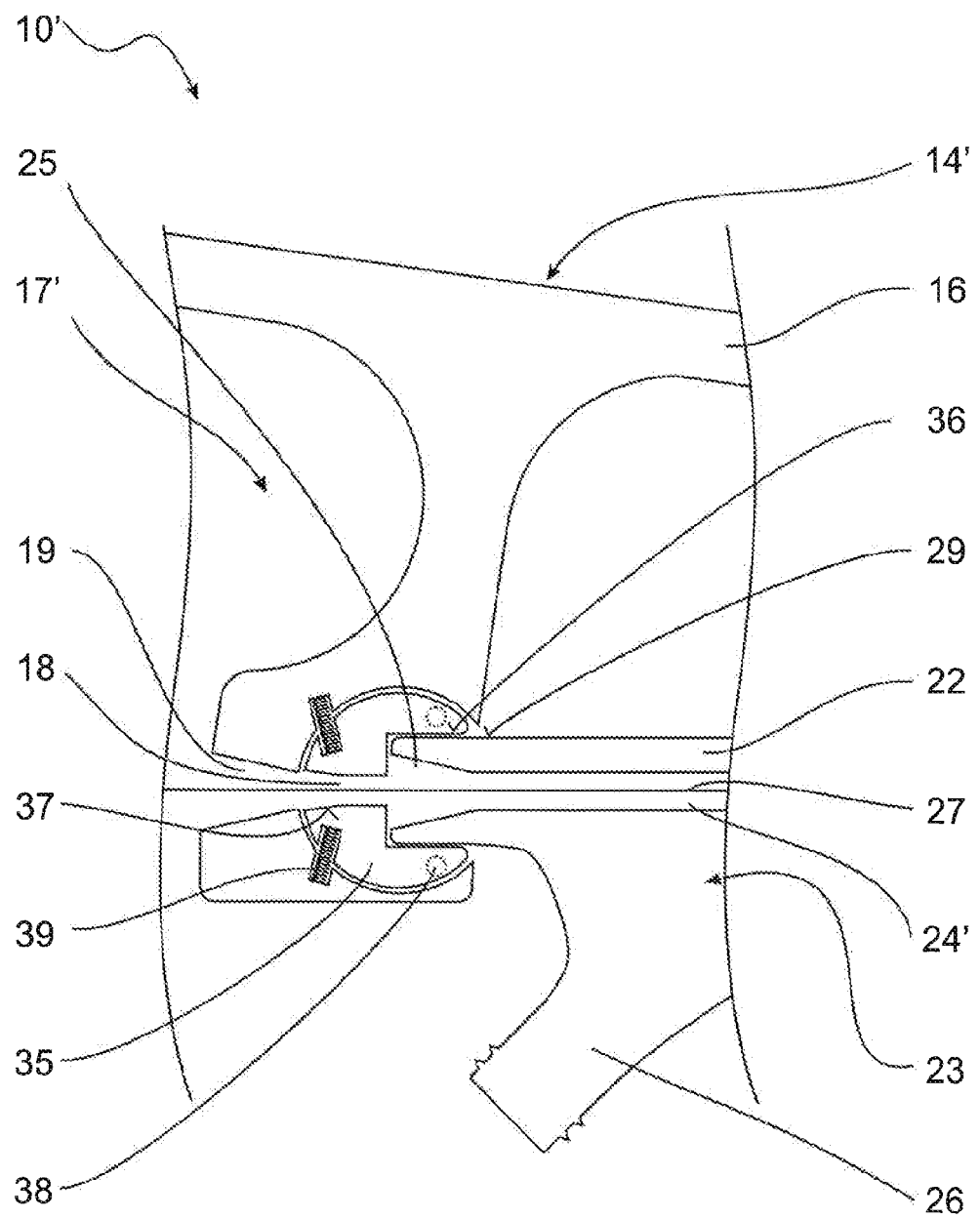
FIG. 10 shows an enlarged schematic drawing of a part of another embodiment of the assembly according to the invention, with the catheter means engaged with the clamping jaws.

FIG. 10 shows a part of another embodiment of assembly 10', with a clamping unit 17' comprising two clamping jaws 35 which comprise surfaces 36, functioning as holding and clamping surfaces, as surface 28 of clamping jaws 21 of the embodiment shown in FIGS. 1 to 9.

In the embodiment shown in FIG. 10, clamping jaws 35 are connected to clamping unit 17' via axes 38, allowing the rotational movement of clamping jaws 35 with respect to clamping unit 17'. Catheter engaging means 23 with its surface 29 engages surfaces 36, forcing apart clamping jaws 35.

The counter-pressure to this movement is exerted by springs 39, pressing the surfaces 36 of clamping jaws 35 against catheter engaging means 23, hence firmly but releasably holding catheter 22 by the clamping unit 17'.

Further, clamping jaws 35 being pressed apart by catheter engaging means 23, leave open clamping lumen 18, comprised in the clamping unit 17'. Thereby, guide wire 27 is not held/clamped by the clamping jaws 35 and can be moved along its longitudinal axis.

Figure 11:
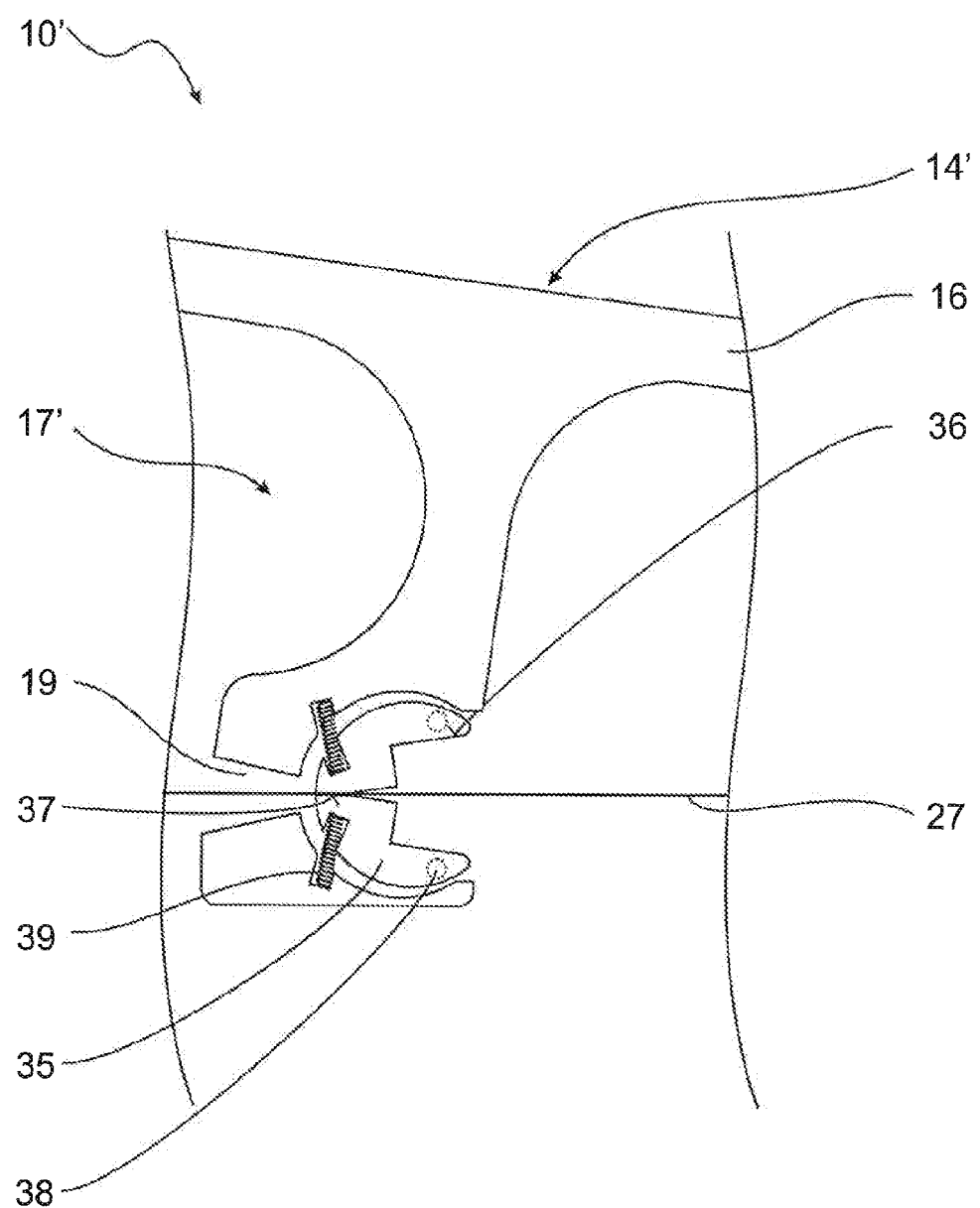
FIG. 11 shows the assembly as in FIG. 10, but with the catheter means having been disengaged from the clamping jaws.

FIG. 11 shows the assembly 10' displayed in FIG. 10, but with catheter engaging means 23 having been disengaged from clamping unit 17. Without the pressure exerted by catheter engaging means 23 when engaged with the clamping unit 17', clamping jaws 35 are forced by springs 39 against guide wire 27, tightly holding guide wire 27 in between their surfaces 37. Thereby, a movement of guide wire 27 in longitudinal direction is prevented.

To summarize, the present invention allows the safe and easy deployment of a catheter into a body lumen, automatically and simultaneously fixating the guide wire used for catheter advancement into the body lumen.

Hence, said guide wire is prevented from further advancement into the body lumen even during catheter advancement, in a efficient way and without further handling or operating steps.

Thus, medical interventions involving appliance of such guide wires and catheters are made more reliable and safe.

What is claimed is:

1. An assembly for inserting a catheter into a body lumen, the assembly comprising
    a guide catheter to be introduced into an aperture of the body lumen,
    an elongate fixing element having a proximal and a distal end, wherein with its distal end the fixing element is securable to the guide catheter, and wherein at the proximal end of the fixing element,
    a clamping device is provided, which clamping device comprises a clamping unit, for securing a guide wire in relation to the guide catheter, and which clamping unit comprises a passageway for the guide wire,
    wherein the assembly comprises the catheter, having a proximal end and a distal end, wherein the proximal end comprises an engaging means for releasably engaging the clamping unit, and
    wherein by engagement of the engaging means of the catheter with the clamping unit the guide wire is movable through the guide catheter and
    wherein, upon disengagement of the engaging means of the catheter from the clamping unit, the guide wire is non-movably secured relative to the guide catheter, and
    wherein said clamping unit comprises at least two clamping jaws for fixing the guide wire, the clamping jaws are separable from one another by frictional engagement of the engaging means of the catheter.

2. The assembly of claim 1, wherein the clamping jaws are separable by elastic deformation of one or more material bridges connecting one of the ends of the clamping jaws, respectively.

3. The assembly of claim 1, wherein the engaging means of the catheter for engaging the clamping unit comprise a proximal and a distal end, wherein the proximal end is adapted for releasably engaging the clamping unit, and wherein via the distal end the means are releasably or non-releasably attached to the catheter.

4. The assembly of claim 3, wherein the proximal end of the engaging means of the catheter for releasably engaging the clamping unit comprises a handling portion of the catheter releasably or non-releasably attached to the catheter.

5. The assembly of claim 1, wherein the engaging means of the catheter for engaging the clamping unit comprise a ring or half-ring shaped element for handling the catheter.

6. The assembly of claim 1, wherein the clamping jaws each comprise a surface configured to frictionally engage the guide wire upon disengagement of the means of the catheter from the clamping unit.

7. The assembly of claim 1, wherein the clamping jaws each comprise a surface configured to frictionally engage the guide wire upon disengagement of the means of the catheter from the clamping unit, and wherein the surfaces comprise a knurled or undulated surface.

8. The assembly of claim 1, wherein the guide catheter comprises a valve.

\* \* \* \* \*